US012302875B2

(12) United States Patent
Yoshioka et al.

(10) Patent No.: US 12,302,875 B2
(45) Date of Patent: May 20, 2025

(54) EGG COLLECTION DEVICE FOR BAGWORM MOTH AND BREEDING METHOD AND EGG COLLECTION METHOD OF BAGWORM MOTH USING THE SAME

(71) Applicants: NATIONAL AGRICULTURE AND FOOD RESEARCH ORGANIZATION, Tsukuba (JP); KOWA COMPANY, LTD., Nagoya (JP)

(72) Inventors: Taiyo Yoshioka, Tsukuba (JP); Ryoko Ichiki, Tsukuba (JP); Tsunenori Kameda, Tsukuba (JP); Takayuki Matsuda, Tsukuba (JP); Atsushi Ito, Tsukuba (JP); Akimune Asanuma, Tsukuba (JP)

(73) Assignees: NATIONAL AGRICULTURE AND FOOD RESEARCH ORGANIZATION, Tsukuba (JP); KOWA COMPANY, LTD., Nagoya (JP)

( * ) Notice: Subject to any disclaimer, the term of this patent is extended or adjusted under 35 U.S.C. 154(b) by 0 days.

(21) Appl. No.: 18/256,568

(22) PCT Filed: Dec. 10, 2021

(86) PCT No.: PCT/JP2021/045524
§ 371 (c)(1),
(2) Date: Jun. 8, 2023

(87) PCT Pub. No.: WO2022/124397
PCT Pub. Date: Jun. 16, 2022

(65) Prior Publication Data
US 2024/0016131 A1 Jan. 18, 2024

(30) Foreign Application Priority Data
Dec. 10, 2020 (JP) .................. 2020-205316

(51) Int. Cl.
*A01K 67/30* (2025.01)
(52) U.S. Cl.
CPC .................. *A01K 67/30* (2025.01)
(58) Field of Classification Search
CPC ...... A01K 67/033; A01K 67/04; A01K 67/00; A01K 2227/706; A01K 2227/70
(Continued)

(56) References Cited

U.S. PATENT DOCUMENTS

2005/0241590 A1   11/2005   Koznarek
2017/0231205 A1*   8/2017   Unger ................. A01K 67/033
                                                            119/6.6
(Continued)

FOREIGN PATENT DOCUMENTS

CN   107279073 A   10/2017
JP   2018-74951 A   5/2018
(Continued)

OTHER PUBLICATIONS

Osaki, Shigeyoshi, "Animals Teach Science on natural Fibers: Spiders Sikls, Bagworm's Silks, and Collagen Fibers", Journal of the Society of Fiber Science and Technology, vol. 58, No. 3, 2002, p. 74-78 and a partial English translation.
(Continued)

*Primary Examiner* — Morgan T Jordan
(74) *Attorney, Agent, or Firm* — Lucas & Mercanti, LLP

(57) ABSTRACT

A simple and efficient breeding method for the bagworm moth is provided, as well as a device for performing the method. Also developed and provided is a method of easily collecting eggs from a bagworm moth, an egg collection device for bagworm moths composed of a tubular container. A bagworm moth breeding method and egg collection method performed using the device are also described.

14 Claims, 6 Drawing Sheets

(58) Field of Classification Search
USPC .................................. 119/6.5, 6.7, 6.6, 270
See application file for complete search history.

(56) References Cited

U.S. PATENT DOCUMENTS

| | | |
|---|---|---|
| 2020/0157706 A1 | 5/2020 | Kameda et al. |
| 2020/0407518 A1 | 12/2020 | Yoshioka et al. |
| 2022/0408705 A1* | 12/2022 | Roche-Bruyn ...... A01K 67/033 |

FOREIGN PATENT DOCUMENTS

| | | |
|---|---|---|
| JP | 2019-44117 A | 3/2019 |
| KR | 20190073891 A | 6/2019 |
| WO | 2019/003364 | 1/2019 |

OTHER PUBLICATIONS

Sawada, Yasuhiro; et al., "Field Parasitism of Bagwork, *Eumeta variegata* (Lepidoptera: Psychidae) by the Newly Invaded Parasitic Fly, *Nealsomyia rufella* (Diptera: Tachinidae) in Kochi Prefecture, Japan", Jpn. J. Ent. (N.S.) vol. 5, No. 4: 111-119, Dec. 25, 2002 and an English Abstract.

Yoshioka, Taiyo; et al., "A study of the extraordinarily strong and tough silk produced by bagworms", Nat Commun 10, 1469 (2019) (11 pages).

ISA/JP, "International Search Report", issued in connection with PCT International Application No. PCT/JP2021/045524, which was mailed Jan. 25, 2022, with English translation (5 pages).

EPO, Supplementary European Search Report, mailed Sep. 10, 2024, issued for the related European patent application No. 21903493. 1, 4 pages.

* cited by examiner

EGG COLLECTION DEVICE FOR BAGWORM MOTH AND BREEDING METHOD AND EGG COLLECTION METHOD OF BAGWORM MOTH USING THE SAME

CROSS-REFERENCE TO RELATED APPLICATIONS

This application is a 371 national phase entry of PCT/JP2021/045524, filed Dec. 10, 2021, which claims the benefit of Japanese Patent application No. 2020-205316, filed Dec. 10, 2020.

TECHNICAL FIELD

The present invention relates to an egg collection device for bagworm moth and a simple and efficient breeding method and egg collection method of bagworm moth using the same.

BACKGROUND ART

A bagworm, which is a larva of a moth belonging to the family Psychidae, spends the whole larval stage living with a spindle-shaped or cylinder-shaped bag nest made of pieces of leaves and twigs assembled by a spun thread, during which the larva usually hides itself inside the nest and moves with the nest even when it eats. In recent years, a bagworm silk thread spun by this bagworm has been attracting attention as an extremely useful novel animal natural fiber (Patent Literature 1 and Non-Patent Literature 1).

To industrialize a bagworm silk thread, it is vital to establish a rearing technology such as the mass rearing and successive rearing of bagworms. However, the bagworm silk thread industry has just begun, and a rearing technology is still under development. Obtaining a bagworm relies exclusively on collection on the field, and this situation results in large obstruction in the industrialization of a bagworm silk thread. Because of this, it is imperative to develop an artificial breeding technology and egg-producing technology for a bagworm moth. It is conceivable to apply, to bagworm rearing, a silkworm rearing technology already established in the sericultural industry, as a silkworm is a larva of the same Lepidoptera. However, the mating mode and egg-laying mode of a bagworm moth are markedly different from those of *Bombyx mori*, and hence, such a silkworm rearing technology is not applicable.

In the case of *Bombyx mori*, natural mating can be induced just by placing a female adult (hereinafter, often referred to as a "female moth") and a male adult (hereinafter, often referred to as a "male moth") both after emergence in a limited space such as a box so that the female moth and the male moth can be in contact with each other. In addition, artificial breeding can also be performed by a hand-pairing method in which the bottoms of the abdomens of a female moth and a male moth are forced to be artificially brought in contact with each other so that mating can be established. Furthermore, when a female moth after mating is placed on a piece of paper, the female moth starts egg-laying on the paper without maturing feeding, and thus, collecting the paper after egg-laying is sufficient for egg collection. This is very easy.

On the other hand, in the case of many species of bagworm moths, the morphology of the adult is markedly different between the female and the male. Male moth of any species has the morphology of a common moth, but a female moth has an extremely peculiar morphology that cannot be recognized as a moth at a glance. In particular, in the case of an evolutionarily new species in Psychidae, such as *Eumeta japonica* or *Eumeta minuscula*, most of the motile organ and sense organ of a female moth are degenerated, and the moth has a maggot-like morphology that has lost a wing, leg, compound eye, tactile sense, mouthparts, and the like (FIG. 1A-a).

In addition, when a bagworm moth undergoes metamorphosis from a larva to a pupa, the bagworm pupates in the nest in which the bagworm has spent its larval stage, without producing a cocoon as a silkworm does. In a nest, a male moth pupates in an upside-down posture with its head toward the bottom of the nest during the prepupal stage. After emergence, the male moth makes a hole in the bottom end of the nest, and goes out thereof. However, a female moth does not take off its puparium after emergence (FIG. 1A-b), also has lost the migrating capability completely, and thus, spends its whole life in its nest without going out into the outside.

Owing to such a special ecology as above-described, the mating mode and egg-laying mode of a bagworm moth are extremely peculiar. A female moth pokes its head out through the opening in the bottom end of the nest, discharges sex pheromone, and attracts a male moth, which reaches the nest in which the female moth lies hidden (FIG. 1B-c). The male moth then inserts its abdomen through the opening of the bottom end of the nest to mate (FIG. 1B-d). However, the mating pore of the female moth is located in the innermost of the nest, and moreover, inside of the puparium. Then, the male moth stretches its abdomen, inserts the abdomen between the abdomen of the female moth and puparium in the nest, and furthermore, finds the mating pore at the tip of the abdomen of the female moth to establish mating (FIG. 1C). After the mating, the female moth lays eggs in the puparium, and the eggs is held in the puparium until hatching.

A bagworm moth can also be artificially bred. However, a method that is used for this is not a hand-pairing method such as for *Bombyx mori*, but merely a method in which the abdomen of a male moth is artificially inserted through the opening of the bottom end of the nest in which a female moth lies hidden (Non-Patent Literature 2). This method not only does not enable to grasp the state of a female moth in the nest, but also does not enable to verify the position of the mating pore of a female moth from the outside of the nest. Thus, this method cannot appropriately attract the mating organ of the male moth to the mating pore of the female moth, causing a problem in that the mating efficiency is very low. In addition, the method does not enable to verify the establishment and termination of the mating by visual observation, thus causing, for example, a problem in that, although the mating is not established yet, pairing is terminated, not making it possible to collect a fertilized egg, or conversely a problem in that forcibly terminating the pairing of the individuals during mating damages the mating pore of the female. Furthermore, the method does not enable to verify egg-laying from the outside of the nest. Thus, the nest of the female moth after breeding has to be cut open to identify an egg batch inside the puparium. There is also a problem in that, if the nest is opened before egg-laying, egg collection cannot be performed again.

CITATION LIST

Patent Literature

Patent Literature 1: WO2019/003364 Non-Patent Literature

Non-Patent Literature 1: Shigeyosi Ohsaki, 2002, Sen'i Gakkaishi (Sen'i To Kogyo), 58: 74-78

Non-Patent Literature 2: Sadahiro Sawada, Ryo Arakawa, 2002, Jpn. J. Ent (NS), 5(4): 111-119

SUMMARY OF INVENTION

Technical Problem

A problem to be solved by the present invention is to develop and provide a simple and efficient breeding method of bagworm moth, and a device for performing the method.

A problem to be solved by the present invention is to develop and provide a method of collecting eggs from a bagworm moth easily, and a method of mass-producing first instar bagworms.

Solution to Problem

To solve the above-described problems, the present inventors have first developed a method of examining the inside of the puparium by fluoroscopy using an X-ray device. This method makes it possible to observe the state in the nest and in the puparium even from the outside of the nest. However, an X-ray device involves very complicated transportation and installation of the device and materials, and besides, requires time and labor until the examination by fluoroscopy is performed. In addition, not only the device cost but also the running cost is very high, and besides, the influence of the X-ray irradiation on a living body or a cell cannot be eliminated. Accordingly, this method cannot be said to be realistic in the performance of a business in terms of efficiency and cost.

Subsequently, the present inventors have attempted forced mating in which a female moth of a bagworm moth is removed from its nest and puparium, and then the female moth and the bottom of the abdomen of the male moth are directly brought in contact. In the case of *Bombyx mori*, mating can be forced to be established by opening the valva at the bottom of the abdomen of a male moth with tweezers or the like, and allowing the valva to hold the bottom of the abdomen of a female moth. However, a male moth of a bagworm moth does not have an organ shaped so as to grasp the abdomen of a female, such as a valva. Accordingly, a hand-pairing method such as for *Bombyx mori* gave an extremely low rate of success in mating.

Because of this, a female moth was removed from the nest, and then, allowed to undergo breeding, holding the puparium. As a result, mating was established with a very high probability. This has revealed that a nest is not necessary for the mating of a bagworm moth, but that it is important that a female moth holds the puparium. In addition, it has also been revealed that this puparium, even if composed of an artificial material, has the same effect as a natural puparium. Because of this, using a pseudo-puparium of a transparent material or an opaque material having a plurality of micropores makes it possible to identify the position of the mating pore of a female moth from the outside, and, through a fine adjustment of the angle and the direction, makes it possible to appropriately attract the mating organ of a male moth to the mating pore of a female moth. Furthermore, it is also possible to verify the establishment and termination of mating and the performance of egg-laying by visual observation. This makes it possible to observe the mating process, and to tremendously enhance the rate of success in mating and the efficiency of egg collection. In addition, placing a removable auxiliary member in an artificial puparium makes it easy to take eggs out of the artificial puparium. Furthermore, having an air hole in the artificial puparium can inhibit eggs in the artificial puparium from generating stuffiness and mold. In addition, the eggs obtained are easy to wash, and thus, ovarial transmission can be prevented by disinfection or sterilization. The present invention is based on these novel findings, and provides the following items.

(1) An egg collection device for bagworm moth composed of a tubular container, comprising: an insert hole having an inner diameter into which a female adult of a bagworm moth fits; a receiving part capable of receiving the whole or part of the abdomen of the female imago; and an egg-holding part configured to hold eggs obtained by egg-laying.

(2) The egg collection device according to (1), wherein the egg-holding part has a ventilating means.

(3) The egg collection device according to (1) or (2), wherein the egg-holding part has, therein, a removable egg-receiving means for receiving and collecting the eggs obtained by egg-laying.

(4) The egg collection device according to (1) or (2), comprising a lid configured to occlude the insert hole.

(5) The egg collection device according to any one of (1) to (3), wherein the whole or part of the tubular container is composed of a transparent material or a translucent material.

(6) The egg collection device according to any one of (1) to (5), wherein the egg-receiving means consists of a thin-layer film composed of a transparent material or a translucent material.

(7) The egg collection device according to any one of (1) to (4), comprising an egg-collecting stand configured such that the egg collection device is placed in the egg-collecting stand in such a manner that the insert hole faces upward.

(8) A breeding method of bagworm moth, comprising: a fitting process of inserting the bottom of the abdomen of a female adult of a bagworm moth into an insert hole of the egg collection device for bagworm moth according to any one of (1) to (7) to fit the abdomen into the insert hole; and a mating process of inserting the bottom of the abdomen of a male adult of a bagworm moth between the insert hole and the abdomen of the female adult to induce mating.

(9) The breeding method according to (8), the female adult of the bagworm moth is an apterous and apodous morphospecies.

(10) The breeding method according to (8) or (9), wherein the female adult is a virgin.

(11) An egg collection method of bagworm moth, comprising: a fitting process of inserting the bottom of the abdomen of a female adult of a bagworm moth separated from a nest and a puparium into an insert hole of the egg collection device for bagworm moth according to any one of (1) to (7) to fit the abdomen into the insert hole; a mating process of inserting the bottom of the abdomen of a male adult of a bagworm moth between the insert hole and the abdomen of the female adult to induce mating; and an egg-laying process of allowing the female adult to lay eggs in the egg-holding part of the egg collection device.

(12) The egg collection method according to (11), further comprising a female-removing process of removing the female individual after the egg-laying process.

(13) A method of producing a first instar bagworm, comprising: an incubation process of incubating, in the egg-holding part, the bagworm moth eggs obtained by the egg collection method of bagworm moth according to (11) or (12); and a first instar bagworm collection process of collecting a first instar bagworm that has harched.

(14) A method of producing a first instar bagworm, comprising: an egg collection process of collecting, from the egg-holding part, the bagworm moth eggs obtained by the egg collection method of bagworm moth according to (11) or (12); and an incubation process of incubating the egg collected.

The present specification encompasses the contents disclosed in the specification and/or drawings of Japanese Patent Application No. 2020-205316, on which the priority of the present application is based.

Advantageous Effects of Invention

A breeding method of bagworm moth using an egg collection device for bagworm moth according to the present invention makes it possible to perform a simple and efficient artificial breeding of a bagworm moth.

A egg collection method of bagworm moth using the egg collection device for bagworm moth according to the present invention makes it possible to obtain a large number of bagworm moth eggs easily.

A method of producing a first instar bagworm of a bagworm moth according to the present invention makes it possible to produce a large number of first instar bagworms easily.

BRIEF DESCRIPTION OF DRAWINGS

FIG. 3A is a picture of a female moth of *Eumeta japonica* placed in an egg collection device for bagworm moth according to the present invention. This picture shows the egg collection device for bagworm moth produced with a 1.5 mL tube that has been improved. FIG. 3B is a picture showing artificial breeding in progress after the bottom of the abdomen of the male moth was inserted between the female moth shown in FIG. 3A and the egg collection device for bagworm moth. FIG. 3C is a picture showing a pair of *Eumeta japonica* moths mating in the egg collection device for bagworm moth according to the present invention. In the picture, the arrow denotes that the mating was established.

FIG. 5A is a picture showing the state in which a large number of *Eumeta japonica* egg batches collected by an egg collection method of bagworm moth according to the present invention are incubated in the egg-holding part of the egg collection device for bagworm moth according to the present invention. FIG. 5B is a picture showing a first instar bagworm of *Eumeta japonica* that was allowed to hatch after the incubating process by a method of producing a first instar bagworm according to the present invention. Besides a large number of first instar bagworms in the egg-holding part of the egg collection device for bagworm moth, the first instar bagworms (arrows) that went out of the egg collection device for bagworm moth are shown. After this, the first instar bagworms are collected in a first instar bagworm collection process. In the egg collection device for bagworm moth in this drawing, a sponge plug is used as a ventilating means.

FIG. 6A is a picture showing one embodiment of the egg collection device for bagworm moth according to the present invention, the device comprising an egg-receiving means. This picture shows the constitution in which a thin-layer film has been pushed as the egg-receiving means into the whole inside of the egg collection device. FIGS. 6B to 6D show female bagworm moth placement (B), egg-laying (C), and egg batch collection (D). FIG. 6E is an enlarged picture of the egg-receiving means detached from the egg collection device for bagworm moth, and shows an egg batch (0604) collected.

DESCRIPTION OF EMBODIMENTS

1. Egg Collection Device for Bagworm Moth 1-1. Overview

A first aspect of the present invention is an egg collection device for a bagworm moth. The egg collection device according to the present invention is composed of a tubular container. The egg collection device according to the present invention not only makes the artificial breeding of a bagworm moth easier to enhance the mating efficiency, but also makes it possible to collect eggs easily and stably.

1-2. Definition of Terms

The following terms frequently used herein are defined.

The term "bagworm moth" collectively refers to a moth belonging to the family Psychidae in the order Lepidoptera. Unless otherwise specified, a bagworm moth as used herein refers to an adult of a bagworm moth, regardless of gender. In addition, a "female adult (individual)" and a "male adult (individual)" as used herein are often referred to as a "female moth" and a "male moth" respectively.

The species of a bagworm moth as a subject in this specification is not limited, and the female moth is preferably an apterous and apodous morphospecies. Here, the "apterous and apodous morphospecies" refers to the species of a bagworm moth that has the morphology of a female moth the wings and legs of which are degenerated. This apterous and apodous morphospecies further comprises a species the sense organs of which, such as a compound eye, a tactile sense, and mouthparts, are degenerated, and the external morphology of which is in maggot-like form. A genus comprising such an apterous and apodous morphospecies is preferably, for example, but not limited to, a species belonging to *Eumeta, Mahasena, Metura, Thyridopteryx*, or the like. Specific examples comprise *Eumeta japonica, Eumeta minuscula, Mahasena aurea*, saunders case moths (*Metura elongatus*), and evergreen bagworms (*Thyridopteryx ephemeraeformis*).

A "bagworm" is a generic term for a larva of a bagworm moth, regardless of the species, gender, and instar. As used herein, a "first instar bagworm" refers to a bagworm that has hatched, but has not undergone the initial ecdysis yet.

As used herein, a "(bagworm) nest" refers to a nest built by a bagworm, and is composed of a silk thread spun by the bagworm itself and of the materials, such as leaves and twigs, which are assembled with the silk thread. The nest is a spindle-shaped, cylinder-shaped, or cone-shaped bag-like nest that can accommodate the whole body of a bagworm. A bagworm moth basically lies hidden in this nest during the larval stage, and in principle, part of the insect body is exposed from the opening of the nest only during eating and migrating. In addition, not only ecdysis but also pupation is performed in the nest. Furthermore, some species of female moths among the bagworm moths live in a nest throughout their lifetime comprising emergence, and mate through the opening at the bottom end of the nest.

Figure 1:
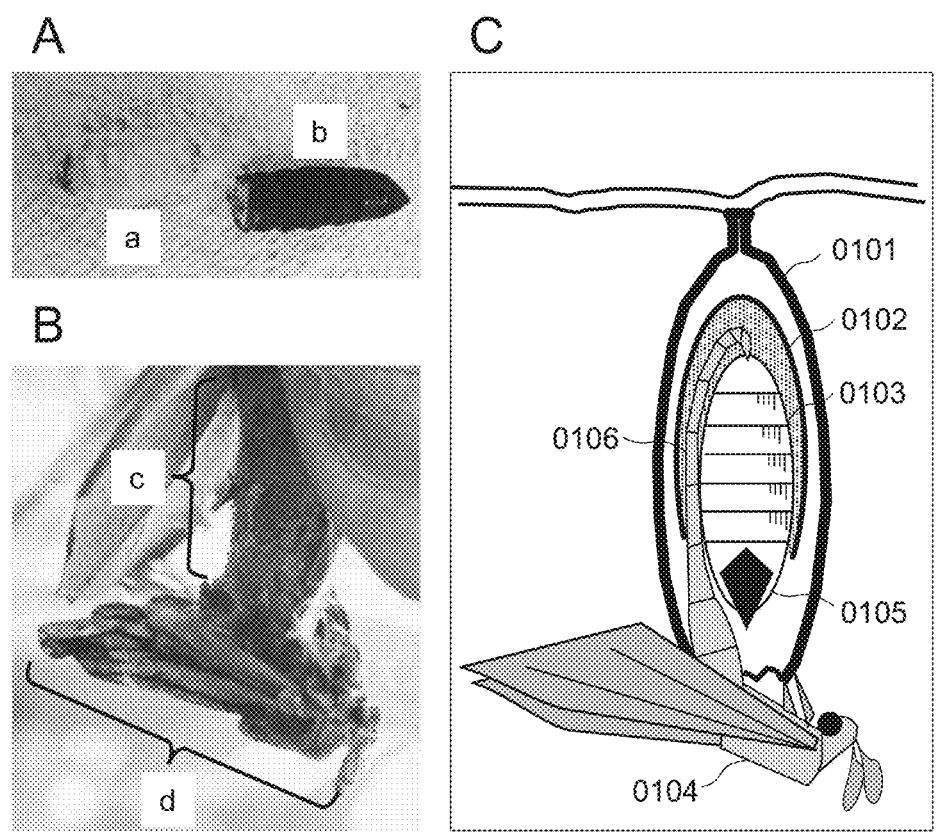
FIG. 1A is a picture showing the morphology (a) of a female moth of *Eumeta japonica* removed from the nest, and showing the puparium (b) of the female moth.
FIG. 1B is an image of *Eumeta japonica* mating on the field. In the picture, c shows a nest with a female moth therein, and d shows a male moth.
FIG. 1C is a schematic view of the inside of the nest in which the female moth of *Eumeta japonica* is mating, as viewed by fluoroscopy. The female moth (0103) of *Eumeta japonica* or the like lies hidden in the puparium (0102) in the nest with its head (0105) facing toward the opening at the bottom of the nest (0101), and spends its whole life in the nest during the larval stage also after emergence. The male moth (0104) can flutter, and is attracted by the sex pheromone discharged by the female moth, finally reaching the nest in which the female moth lies hidden. The male moth that has reached the nest of the female moth inserts the abdomen (0106) into the nest through the opening at the bottom of the nest, stretches the abdomen to find the mating pore at the bottom of the abdomen of the female moth in the innermost of the puparium, and inserts the mating organ into the mating pore to establish mating.

As used herein, a "puparium" refers to the theca present during the pupal stage. Unless otherwise specified, a puparium as used herein refers to the puparium of a bagworm moth. The puparium is composed of cuticles, and, as shown in FIG. 1A-b, is rigid, holding the original spindle-like shape also after the bagworm moth has undergone emergence, and gone out. The puparium of an insect is usually thrown away after emergence, but some species of female moths among the bagworm moths make an opening through which the head and part of the thorax can be exposed even after emergence, and then, stay inside the puparium without taking off the puparium. In addition, a bagworm moth having such ecology uses the puparium as an egg-laying bed, and a female moth lays eggs in the puparium.

1-3. Constitution

Figure 2:
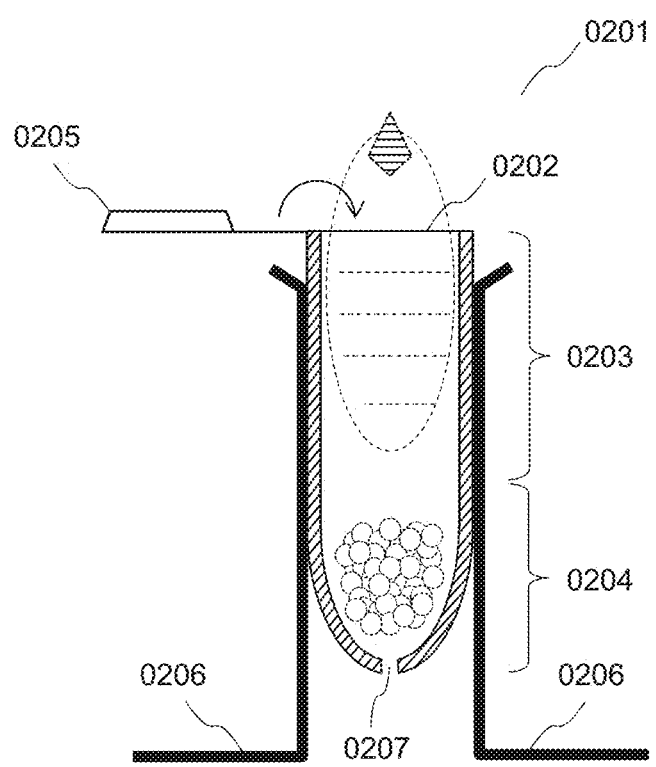
FIG. 2 is a schematic view of an egg collection device for bagworm moth according to the present invention. The female moth placed in the egg collection device for bagworm moth according to the present invention and an egg batch obtained by egg-laying are shown by dashed lines.

The constitution of the egg collection device according to the present invention is shown in FIG. 2. As shown in this drawing, the egg collection device for bagworm moth (0201) according to the present invention comprises an insert hole (0202), a receiving part (0203), and an egg-holding part (0204) as essential constituents, and comprises a lid (0205) or an egg-laying stand (0206) as an optional constituent. Below, each constituent will be specifically described.

1-3-1. Egg Collection Device for Bagworm Moth (1) Structure

The egg collection device for bagworm moth (0201) according to the present invention is composed of a tubular container. As used herein, the "tubular container" refers to a container having a tubular shape, and comprising an internal space that can receive a female adult of a bagworm moth. In addition, in the egg collection device for bagworm moth, at least one end of the tubular container has an opening, and the internal space is in contact with the outside via the opening.

The external shape of the egg collection device for bagworm moth is not particularly limited as long as the external shape is a tubular shape comprising the below-described receiving part (0203), egg-holding part (0204), and insert hole (0202). For example, the external shape may be: a paralleled tubular shape (for example, a columnar shape or a prismatic shape) in which the short-axis cross-section of the egg collection for bagworm moth device is substantially the same all along; a conical or pyramidal shape (for example, a spindle-like shape, a conical shape, or a pyramidal shape) in which the short-axis cross-section is gradually decreased toward an end; or a combination thereof. Here, the "short-axis cross-section" refers to a cross-section comprising the short axis perpendicular to the long axis of the egg collection device for bagworm moth. The external shape of the egg collection device for bagworm moth according to the present invention is preferably a shape the same as or similar to a natural puparium, considering that the egg collection device for bagworm moth is an artificial puparium made to imitate the puparium of a bagworm moth, except when the natural puparium of a bagworm moth itself is used. Examples of the shape comprise a spindle-like shape (comprising a generally spindle-like shape) or a conical shape (comprising a generally conical shape). Alternatively, the egg collection device for bagworm moth may have a branched tubular structure. In this case, the end of each branch can comprise the receiving part (0203), the egg-holding part (0204), and the insert hole (0202).

The egg collection device for bagworm moth is not limited to any particular size. The length in the long-axis direction differs, depending on the species of a bagworm moth to be used, the size of the individual, and the length of the constituent part. The length may be suitably determined, taking into account the length of each of the below-described receiving part (0203) and egg-holding part (0204). The length may usually be 1.5 cm or more, 2.0 cm or more, 2.5 cm or more, 3.0 cm or more, 3.5 cm or more, 4.0 cm or more, or 4.5 cm or more, and 10 cm or less, 9 cm or less, 8 cm or less, 7 cm or less, 6.5 cm or less, 6.0 cm or less, 5.5 cm or less, or 5.0 cm or less. On the other hand, the length in the short-axis direction, that is, the width (outer diameter) of the egg collection device for bagworm moth differs, depending on the species of a bagworm moth to be used, the size of the individual, and the constituent part. The length may suitably be determined, taking into account the size of each of the below-described insert hole (0202), receiving part (0203), and egg-holding part (0204). In addition, the width of the egg collection device for bagworm moth does not need to be uniform all along like a cylindrical shape. As with the spindle type shown in FIG. 2, the width may vary to shorten gradually from the upper portion toward the bottom portion of the egg-holding part. The insert hole needs to have an inner diameter into which the abdomen of a female bagworm moth to be received can fit, and in addition, the receiving part needs to have an inner diameter that can receive the abdomen of the female moth, and accordingly, the width of the egg collection device for bagworm moth needs to be at least longer than the insert hole and the receiving part. Without limitation, for example, in the case of a large-sized species such as *Eumeta japonica*, the width may range from 4 mm to 19 mm, range from 5 mm to 18 mm, range from 6 mm to 17 mm, or range from 7 mm to 16 mm. In the case of a medium-sized species such as *Eumeta minuscula*, the width may range from 3 mm to 15 mm, from 4 mm to 12 mm, or from 5 mm to 10 mm.

The egg collection device for bagworm moth is not limited to any thickness. The thickness may suitably be determined, taking into account the production cost, the rigidity of the material, and the like. For example, the average thickness may be 0.5 mm or more, 0.6 mm or more, 0.7 mm or more, 0.8 mm or more, 0.9 mm or more, 1.0 mm or more, 1.2 mm or more, or 1.5 mm or more. The width is preferably 3.0 mm or less, 2.8 mm or less, 2.5 mm or less, 2.2 mm or less, or 2.0 mm or less. In addition, the whole device may have a uniform thickness, or may have a thickness different from part to part.

(2) Material

The egg collection device for bagworm moth is not limited to any particular material. The material may be composed of a natural material, an artificial material, or a combination thereof. Here, examples of the natural material comprise the puparium of a bagworm moth itself, metals (encompassing an alloy), minerals, animal-derived materials (encompassing bone, tooth, tusk, shell, scale, and horn), plant-derived materials (encompassing wood, bamboo, stem, and pieces of plant), and the like. Examples of the artificial material comprise synthetic resins (encompassing a thermoplastic resin, a thermosetting resin, and a synthetic rubber), ceramic ware (encompassing ceramics and enamel), glass, paper, carbon fiber, and the like. In addition, examples of the synthetic resin comprise polyethylene, polypropylene, polystyrene, vinyl acetate, cellulose acetate, acrylic resin, polycarbonate, and the like.

It is preferable that the material of the egg collection device for bagworm moth is wholly or partially composed of a transparent material or a translucent material. This is because such a material makes it possible to verify, by visual observation from the outside, the position of the mating pore of a female moth received in the egg collection device for bagworm moth, the establishment and termination of mating, and any or no egg-laying.

As use herein, a "transparent material" refers to a material having a very high light-transmittance quality. This quality makes it possible to see the opposite side through the material. Specific examples of the transparent material comprise glass, polyethylene, polystyrene, polycarbonate, acrylic resin, and the like.

As used herein, a "translucent material" refers to a material having a light-transmitting quality. Despite having a lower light transmittance than a transparent material, such a translucent material makes it possible to sufficiently verify the state of the opposite side through the material. Specific examples of the translucent material comprise, but are not limited to, polypropylene and the like.

On the other hand, even if the material is opaque or not translucent, providing micropores in the receiving part (0203) and/or egg-holding part (0204) of the egg collection device makes it possible to visually observe, from the outside, a female moth received in the same manner as with a transparent material or the like, and simultaneously to enhance the ventilation in the receiving part and the egg-holding part. The diameter of a pore of such a microporous material may be 10 nm to 500 μm, 12 nm to 400 μm, 15 nm to 300 μm, 18 nm to 200 μm, 20 nm to 150 μm, 25 nm to 120 μm, or 30 nm to 100 μm. The number of pores is not limited. The number may suitably be determined, taking into account the shape, size, rigidity, and degree of inside visibility of the receiving part and egg-holding part of the egg collection device.

Examples of a tubular container that has the above-described shape, size, and material, and can be utilized as the egg collection device for bagworm moth comprise a 1.5 mL tube, a conical tube, a centrifuge tube, and the like.

1-3-2. Insert Hole

The "insert hole" (0202) is a pore opened in the tubular container in the egg collection device for bagworm moth to receive a female moth in the below-described receiving part (0203). A female bagworm moth after emergence opens a pore in the head side of the puparium to enable part of the body to be exposed out of the puparium. In the egg collection device for bagworm moth having an artificial puparium, the insert hole is a pore made to imitate the opening.

The insert hole has an inner diameter that fits the abdomen of a female bagworm moth. The insert hole is configured to be capable of holding part of the abdomen of a female moth to be inserted into the receiving part. This inner diameter is approximately the same as the diameter of the opening of the puparium of a female moth in nature. An inner diameter the same as the width of the abdomen of a female moth to be received is usually sufficient. The "width of the abdomen of a female moth" is a width of a cross-section comprising the short axis perpendicular to the long axis of the abdomen of a female moth. However, the width of the abdomen of a female moth is not constant because of the vermicular movement due to expansion and shrinkage during mating and egg laying. Accordingly, the inner diameter of the insert hole may be the same as the average width of the abdomen of a female moth. The "average width of the abdomen of a female moth" refers to the average width of the abdomen calculated from the width of the abdomen during the expansion of the abdomen of a female moth and the width of the abdomen during the shrinkage. This average width of the abdomen has only to enable the abdomen of a female moth to be fitted into the insert hole, and thus, does not need to be strict, but may be an approximate figure. The average width of the abdomen of a female moth is preferably a width determined immediately before the female moth is received in the egg collection device for bagworm moth. The average width of the abdomen of a female moth differs, depending on the species and individual of a bagworm moth, and thus, may be suitably determined in accordance with a female bagworm moth to be used. Without limitation, for example, in the case of *Eumeta japonica*, the width is 3.0 mm to 15.0 mm, 4.0 mm to 12.0 mm, or 5.0 mm to 9.0 mm, and in the case of *Eumeta minuscula*, 2.0 mm to 13.0 mm, 2.5 mm to 12.5 mm, or 3.0 mm to 12.0 mm. Accordingly, the inner diameter of the insert hole of a egg collection device for bagworm moth according to the present invention may be brought in the range of approximately 9.0 mm±4.0 mm, 9.0 mm±3.0 mm, or 9.0 mm±2.0 mm in the case of use of *Eumeta japonica*, and, in addition, in the range of approximately 7.5 mm±5.5 mm, 7.5 mm+4.0 mm, 7.5 mm+3.0 mm, or 7.5 mm+2.0 mm in the case of use of *Eumeta minuscula*.

The shape of the insert hole is not limited. Considering that the cross-section of the abdomen of a female moth in the present invention is generally circular or generally elliptical, it is preferable that the shape of the insert hole to fit to the cross-section is likewise generally circular or generally elliptical.

1-3-3. Receiving Part

The "receiving part" (0203) is a part that can receive the abdomen of a female moth inserted through the insert hole (0202). The receiving part is an essential constituent in the egg collection device for bagworm moth (0201), and has an internal space for receiving a female moth. In the egg collection device for bagworm moth having an artificial puparium, this internal space is made to imitate the space inside the puparium in which a female moth lies hidden after emergence. In the egg collection device for bagworm moth, the receiving part comprises an opening as the insert hole, and in addition, is linked to the below-described egg-holding part (0204).

As use herein, the term "receive" refers to place the whole or part of the abdomen of a female bagworm moth in the internal space.

The receiving part is not limited to any particular shape. Considering that the artificial puparium is made to imitate the inside of a puparium, as above-described, the shape is preferably, for example, cylindrical. The inner diameter of the receiving part is not limited, and is preferably equal to or smaller than the maximum width of the abdomen of a female moth to be received.

The internal space of the receiving part preferably has a shape and a size that at least enable the abdomen of a female moth received to move vermicularly.

On the other hand, the length of the long axis of the receiving part may be equal to or greater than the length of the abdomen of a female moth to be received. For example, when ¾ of the abdomen of a female moth is received in the receiving part, the length of the long axis may be equal to or greater than the ¾ length of the abdomen. In addition, when the whole abdomen of a female moth is received, the length of the long axis may be equal to or greater than the whole length of the abdomen. Accordingly, the length of the long axis of the receiving part differs, depending on the species of a bagworm moth, and may be determined, suitably taking into account the whole length of the abdomen of the species of female moth which is to be received. For example, the whole length of the abdomen of a female moth of *Eumeta japonica* ranges from 10.0 mm to 30.0 mm, from 12.0 mm to 26.0 mm, from 14.0 mm to 24.0, or 16.0 mm to 22.0 mm, and the whole length of the abdomen of a female moth of *Eumeta minuscula* ranges from 5.0 mm to 26.0 mm, from 14.0 mm to 24.0, or from 16.0 mm to 22.0.

1-3-4. Egg-Holding Part

The "egg-holding part" (0204) is a part configured to hold eggs after egg laying. The egg-holding part is an essential constituent of the egg collection device for bagworm moth (0201), and is linked and integrally formed with the receiving part (0203). However, both of them may be separable, and in addition, may be composed of a material different from the material of the receiving part.

The egg-holding part provided below the receiving part, that is, at the bottom of the egg collection device for bagworm moth holds and stores the eggs at least until the completion of the egg laying by a female moth or until the hatch.

The egg-holding part is not limited to any particular size as long as the internal space of the egg-holding part is sized enough to hold the eggs. The length of the internal space may have a size, for example, 2 mm or more, 3 mm or more, 5 mm or more, 10 mm or more, or 15 mm or more, and 30 mm or less, 25 mm or less, or 20 mm or less. Accordingly, the length of the egg-holding part may be equal to or greater than the length of the internal space.

When the receiving part and the egg-holding part are integrally formed, receiving a female moth in the receiving part usually results in leaving a surplus space several millimeters or more from the tail end of the female moth to the bottom of the egg collection device. This surplus space may be used as the internal space of the egg-holding part.

The egg-holding part is not limited to any particular shape as long as the egg-holding part can hold the eggs. The container may have, for example, a conical shape, a pyramidal shape, or a round-bottomed shape.

The egg-holding part may comprise an egg-receiving means as an optional means. The "egg-receiving means" is a means that functions to receive eggs after egg laying in the egg-holding part, and collect the eggs from the egg collection device for bagworm moth. The means is placed in the egg-holding part, and is configured to be removable from the egg-holding part.

The egg-receiving means is not limited to any shape. The shape may be bag-like along the shape of the inside of the egg-holding part or the inside of the egg collection device for bagworm moth, may be in the form of a sheet pushed into the egg-holding part when used, or may be a combination thereof. For example, a sheet-like egg-receiving means is convenient because such a means has only to be pulled out from the upper portion of the egg-holding part or the upper portion of the egg collection device for bagworm moth, and spread to enable an egg batch inside the egg-holding part to be collected easily.

The egg-receiving means is not limited to any particular form, and may usually be a thin-layer film, fabric, unwoven fabric, net, or a combination thereof so as to enable the space inside the egg-holding part to be maintained. In the case of a thin-layer film, the film may have one or a plurality of pores.

The egg-receiving means is not limited to any material. Examples of the material include synthetic resins (plastic and synthetic rubber), natural resins (natural rubber), cellulose (paper and plant fiber), animal fibers (fur, silk thread, hide, collagen, and gelatin), glass (glass fiber), and carbon fiber, and the like. In addition, the material is preferably a transparent material or a translucent material that makes it possible to verify any or no egg laying or the state of the inside of the egg-holding part. The food-packaging wrap film has excellent transparency, and is particularly suitable. Examples of a known material for a food wrap film comprise, but are not limited to, polyvinylidene chloride (PVDC), polyvinyl chloride (PVC), polyethylene (PE), and polymethylpentene (PMP).

Figure 6:
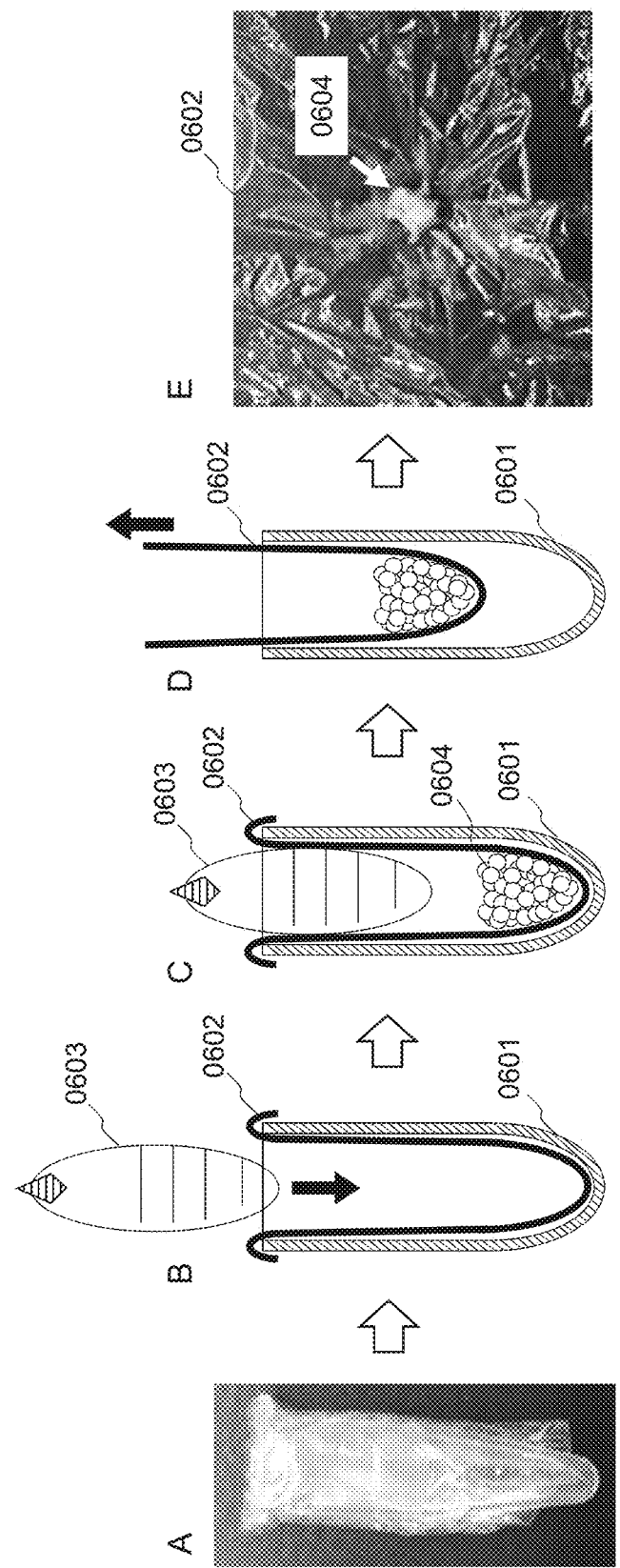
FIG. 6 illustrates schematic views showing the constitution of an egg-receiving means in the egg collection device for bagworm moth according to the present invention, and showing the use of the means.

A specific example of the constitution of the egg-receiving part is shown in FIG. 6. FIGS. 6A and 6B in this drawing show an egg collection device for bagworm moth (0601) in which the egg-receiving means (0602) composed of a thin-layer film is placed in the whole inside comprising the egg-holding part. As shown in FIGS. 6B and 6C, a female individual (0603) of a bagworm moth is inserted into this egg collection device for bagworm moth, allowed to mate with a male individual, and then allowed to lay eggs in the egg-holding part. The egg batch (0604) obtained is collected by removing the female individual after egg laying, and then pulling the egg-receiving part (0602) upward, which is thus separated from the egg collection device for bagworm moth (0601), as shown in FIG. 6D. After being separated, the sheet-like egg-receiving part (0602) is spread, as shown in FIG. 6E, so that the egg batch (0604) can be collected easily.

The egg-holding part may comprise a ventilating means (0207) as an optional means. The "ventilating means" is an opening provided to secure ventilation in the internal space of the egg-holding part. The ventilating means is constituted by one or a plurality of pores and/or slits open to the outside. When the opening is a pore, the pore is not limited to any size, and the maximum width of the pore is preferably smaller than the diameter of an egg to function to hold the eggs. In addition, in the case of a slit, the slit is not limited to any length or any width, and the maximum width of the slit is preferably smaller than the diameter of an egg as with the pore. When a pore or slit having the maximum width larger than the diameter of an egg is provided, the pore or slit is desirably occluded with an air-permeable material, for example, a filter, mesh, sponge, or the like, to prevent the falling of eggs, the escape of a first instar bagworm after hatching, and the like. In addition, the egg-holding part itself may be composed of an air-permeable material.

Comprising a ventilating means makes it possible to avoid a temperature rise and excessive humidity in the egg-holding part. As a result, it is possible to prevent an event having an undesired influence on the developmental stage of eggs, such as the decomposition of an egg and the generation of mold that are due to stuffiness and the like.

1-3-5. Lid

The "lid" (0205) is an optional constituent in the egg collection device for bagworm moth (0201), and is a part that occludes the insert hole (0202). A lid that occludes the insert hole is not always necessary. However, comprising the lid makes it possible to prevent an egg in the egg-holding part from being dried excessively by removing a female moth after egg laying, and opening the insert hole, and to prevent a first instar bagworm after hatching from escaping.

The lid is not limited to any particular shape, size, or material as long as the lid can occlude the insert hole. For example, the lid may have a width equal to or greater than the diameter of the insert hole, and has a length equal to or smaller than the length of the receiving part. The material may be an air-impermeable material, for example, natural rubber, synthetic resin, or the like, but is preferably an air-permeable material. Examples of the material comprise porous materials (sponge), filters, plant materials (paper and the like), balls of thread (balls of cotton, balls of hemp, balls of wool, balls of silk, and the like). The structure for occluding the insert hole is not limited. The structure may be a push-in type, such as a cork stopper or a rubber stopper, or may be a screw type, such as a screw cap.

The lid may be integrally formed with the egg collection device for bagworm moth, or may be a separate type that is removable.

1-3-6. Egg-Collecting Stand

The "egg-collecting stand" (0206) is an optional constituent of the egg collection device for bagworm moth (0201), and is a stand in which the egg collection device is placed and fixed in such a manner that the insert hole (0202) of the egg collection device for bagworm moth faces upward.

Here, the word "upward" means that the insert hole of the egg collection device for bagworm moth is at more than 0 degrees and 90 degrees or less with respect to the horizontal plane. It is preferable that the insert hole is at 45 degrees to 90 degrees, 60 degrees to 90 degrees, 70 to 90 degrees, 80 to 90 degrees, or 85 to 90 degrees with respect to the horizontal plane. The insert hole is suitably at 80 to 90 degrees.

In nature, the puparium of a bagworm moth is opened downward. The bottom of the puparium is above the opening, and thus, an egg batch laid in the puparium can fall from the opening if left as it is. Because of this, a female moth covers and binds the surface of the eggs with its own scales to prevent the eggs from falling after egg laying, occludes the opening of the puparium with its own body, strives to protect the eggs, dies immediately before hatching, and falls from the nest. A hatched first instar larva goes out into the outside via the opening made in the puparium and the opening at the lower portion of the nest.

On the other hand, in the egg collection device for bagworm moth according to the present invention, the direction of the insert hole can be set freely. That is, placing the egg-collecting stand so that the egg-holding part corresponding to the bottom of the puparium can be placed facing upward has a great advantage in that an egg batch does not fall through the insert hole without covering and binding the surface with the scales of a female moth and without the presence of a female moth.

The egg-collecting stand may be integrally formed with the egg collection device for bagworm moth, or may be a separate type that is removable. Examples of the separate type comprise a rack, stand, or case in which one or more egg collection device for bagworm moth can be placed and held in an upright position or a slanted position.

2. Breeding Method of Bagworm Moth

2-1. Overview

A second aspect of the present invention is a breeding method of bagworm moth. The method according to the present invention artificially establishes the mating of a bagworm moth, using the egg collection device for bagworm moth according to the first aspect. The method according to the present invention makes it possible to solve a problem with a conventional artificial breeding method of bagworm moth, and to establish the mating of a bagworm moth easily and efficiently.

2-2. Method

A b breeding method of bagworm moth according to the present invention comprises a fitting process and a mating process as an essential process. Each process will be described below.

2-2-1. Fitting Process

Figure 3:
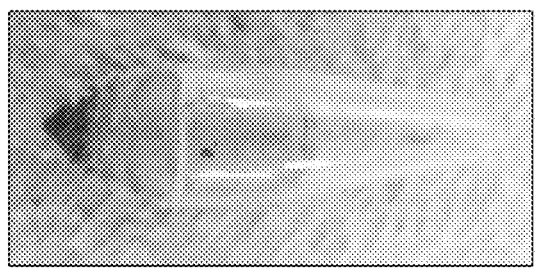
FIG. 3 illustrates pictures showing artificial breeding of *Eumeta japonica* using the egg collection device for bagworm moth according to the present invention.
Figure 3:
Figure 3:

The "fitting process" is a process of inserting a female bagworm moth through the insert hole of the egg collection device for bagworm moth according to the first aspect. This process fits the abdomen of a female moth into the insert hole (FIG. 3A).

A female moth to be used in the method according to the present aspect is an individual before egg-laying. The individual is desirably a virgin. The bagworm moth is not limited to any species, and is suitably an apterous and apodous morphospecies a female moth of which has a maggot-like morphology.

In the present process, a naked female moth separated from the nest and the puparium is used. A method of separating a female moth from the nest and the puparium is not particularly limited. Examples of the method comprise a method in which a nest in which a female moth lies hidden is cut open with scissors or the like without damaging the female moth; the opening of the puparium is broken wide-open; and then, the female moth is withdrawn using tweezers or the like. Alternatively, it is also possible that a pupa is removed from the nest during the pupal stage, and then allowed to wait for emergence, whereafter a female moth undergoes emergence and opens a pore in the puparium, and then the female moth is removed from the nest by the above-described method.

The female moth made naked may be inserted through the insert hole of the egg collection device for bagworm moth, and pushed in until the abdomen is fitted into the insert hole.

2-2-2. Mating Process

The "mating process" is a process of artificially inserting the bottom of the abdomen of a male moth into the egg collection device for bagworm moth after the fitting process, and then inducing mating between a female bagworm moth and a male bagworm moth. The present process establishes the mating of the bagworm moths.

A male moth to be used in the method according to the present aspect is the same species of bagworm moth as a female moth used in the fitting process. The male moth may be either a virgin individual or a mated individual. A male moth can mate with a female moth a plurality of times, and hence, a male moth used once for artificial breeding can be used again for artificial breeding with another female moth.

After the fitting process, the bottom of the abdomen of the male moth is inserted artificially between the abdomen of a female moth fitted and fixed in the egg collection device for bagworm moth and the insert hole. The inserting method is not limited. For example, with a male moth in a hand, the bottom of the abdomen of the male moth may be inserted between the abdomen of a female moth and the insert hole (FIG. 3B). Then, the male moth that has inserted the abdomen stretches the abdomen by itself, finds the mating pore of the female moth, and establishes mating (FIG. 3C). When the male moth cannot find the mating pore of the female moth successfully, the male moth may be attracted toward easier mating by finely adjusting the direction of the male moth and the position of inserting, using a hand or the like. In this case, an egg collection device for bagworm moth composed of a transparent material or a translucent material is convenient because such the device enables the state of the inside to be more easily verified by visual observation.

2-3. Effect

The breeding method of bagworm moth according to the present invention makes it possible to grasp the state of a female moth, unlike a conventional method. In addition, using the egg collection device of a transparent material or the like not only makes it possible to appropriately attract the mating organ of a male moth to the mating pore of a female moth, but also makes it possible to verify the establishment and termination of the mating by visual observation, thus making it possible to enhance the mating efficiency tremendously.

3. Egg Collection Method of Bagworm Moth 3-1. Overview

A third aspect of the present invention is an egg collection method of bagworm moth. The method according to the present invention is a method of obtaining a large number of eggs from a bagworm moth, using the egg collection device for bagworm moth according to the first aspect. The method according to the present invention makes it possible to obtain a large number of bagworm moth eggs easily and stably.

3-2. Method

An egg collection method of bagworm moth according to the present invention comprises a fitting process, a mating process, and an egg-laying process as essential processes, and in addition, comprises a male moth removal process and a female moth removal process as optional processes. Among these, the fitting process and the mating process are the same as the fitting process and the mating process in the breeding method of bagworm moth according to the second aspect. That is, the egg collection method of bagworm moth according to the present aspect is a method performed subsequently to the breeding method of bagworm moth according to the second aspect. In view of this, the description of the processes detailed in the second aspect is omitted here, and the egg-laying process and the male moth removal process that are characteristic of the present aspect will be described below.

3-2-1. Male Moth Removal Process

The "male moth removal process" is a process of removing a male individual after the mating process. This process is an optional process in the egg collection method of bagworm moth, and, if necessary, precedes the following egg-laying process.

A male moth usually terminates mating spontaneously after the mating process, places back the abdomen stretched, and then leaves a female moth. Accordingly, the male moth may be left as it is after the mating process until the following egg-laying process. On the other hand, the male moth can be artificially separated and removed in the present process. In this case, the mating organ of the male moth and the mating pore of the female moth are separated, the termination of mating is verified, and then, the male moth is forcibly removed before leaving spontaneously. For the male moth to be removed, the abdomen of the male moth may be withdrawn carefully without allowing the female moth to come off from the egg collection device for bagworm moth, and then pulled off from the egg collection device for bagworm moth. The male moth separated can be used again in a mating process with another female moth as above-described.

3-2-2. Egg-Laying Process

The "egg-laying process" is a process of egg-laying in the egg-holding part of the egg collection device after the mating process. This process is an essential process in the egg collection method of bagworm moth, and is performed after the mating process or after the subsequent male moth removal process as an optional process. The temperature and humidity conditions during the periods from the establishment of breeding to the start of egg-laying and during the egg-laying are not very strict, and not particularly limited as long as the conditions are in the temperature range of activity of a bagworm moth. The temperature and the humidity may preferably be in the range of from 20 to 25° C. and in the range of from 45 to 70% respectively.

If left to stand without any special treatment, the female moth after the mating starts egg-laying within 24 hours after the mating, and the eggs laid are held as they are in the form of an egg batch in the egg-holding part. A female moth lays approximately 1,000 to 3,000 eggs at a time, and the eggs form egg batches. Collecting these egg batches makes it possible to obtain a large number of bagworm moth eggs easily, the eggs being conventionally difficult to obtain efficiently and stably.

In addition, the present process makes it possible to collect the eggs as they are, and makes it easier to perform an egg washing treatment, which is conventionally difficult. Through this treatment, disinfection and sterilization can be performed. Hence, even when a female parent moth is infected with bacteria or viruses, it is possible to prevent vertical transmission from the female parent moth and horizontal transmission due to contact between eggs.

Furthermore, using a transparent material or a translucent material as a material for the egg collection device for bagworm moth makes it possible to accurately grasp the amount of egg-laying in number. The eggs laid can be preserved as they are in the egg-holding part without being collected.

3-2-3. Female Moth Removal Process

The "female moth removal process" is a process of removing a female moth remaining in the egg collection device for bagworm moth after the egg-laying process. This process is an optional process in the gg collection method of bagworm moth, and, if necessary, can be performed after the egg-laying process.

The female moth that has finished egg-laying covers and binds the surface using its own scales so that the eggs cannot fall. In addition, the female moth itself works as the lid of the opening of the puparium until immediately before hatching to retain the egg batch inside the puparium and simultaneously prevent the egg batch from falling through the opening. The female moth used in the egg collection device for bagworm moth according to the present invention also works, by itself, as a lid that occludes the insert hole after egg-laying, but in the egg collection device for bagworm moth, the egg batch does not fall through the insert hole, and hence, the female moth itself does not need to work as a lid.

Because of this, in the present process, the insect body of the female moth made no use after egg-laying is removed from the egg collection device for bagworm moth. The removing method is not limited. For example, the female moth may be picked out of the egg collection device for bagworm moth, using tweezers or the like. On the insert hole through which the female moth has been removed, the lid part is mounted, if necessary.

3-3. Effect

The egg collection method of bagworm moth according to the present invention makes it possible to allow a female moth to lay eggs efficiently after mating, and in addition, to make the verification of egg-laying and the collection of eggs extremely easier than a conventional method.

4. Method of Producing First Instar Bagworm

4-1. Overview

A fourth aspect of the present invention is a method of producing a first instar bagworm. The method according to the present invention makes it possible that bagworms, which are hitherto obtained in substantial numbers by no method other than collection on the field, are simply and stably obtained in the form of first instar bagworms in large numbers. This makes it possible to achieve the mass rearing and successive rearing of bagworms.

4-2. Method

The method according to the present aspect is performed by any one of (1) a method using the egg collection device for bagworm moth or (2) the method of collecting a bagworm moth egg from the egg collection device for bagworm moth, both methods being below-described.

(1) Method Using Egg Collection Device for Bagworm Moth

This method is a method in which a bagworm moth egg obtained by the egg collection method of bagworm moth in the third aspect using the egg collection device for bagworm moth according to the first aspect is controlled in the egg-holding part of the egg collection device for bagworm moth until hatching, and the bagworm after hatching is collected during the first instar stage.

This method comprises an incubating process and a first instar bagworm collection process as essential processes.

(1-1) Incubating Process

The "incubating process" is a process of incubating a bagworm moth egg batch. The incubation temperature is not particularly limited as long as the temperature maintains or facilitates the development of an egg. The bagworm moth egg can usually develop in the range of from 15° C. to 35° C. Accordingly, the temperature may be in this range. For example, the temperature may range from 18° C. to 32° C. or from 20° C. to 30° C.

Eggs to be incubated in the present process are in the form of an egg batch obtained by the egg collection method of bagworm moth in the third aspect, and are incubated as they are in the egg-holding part of the egg collection device for bagworm moth used for egg collection. The incubation may be performed in a room in which the egg collection device for bagworm moth is placed, or in an incubator set at a predetermined temperature.

The incubation period is not limited, and may usually be a period from egg laying to the hatch. The period from egg-laying to hatch can vary, depending on the species of a bagworm moth and the conditions for hatching. Without limitation, for example, when the incubation is performed at the predetermined temperature, the period in the case of *Eumeta japonica* is generally 14 days to 30 days, for example, 17 days to 26 days, and in addition, the period in the case of *Eumeta minuscula* is generally 11 days to 30 days, for example, 14 days to 27 days.

Using a transparent material or a translucent material as a material for the egg collection device for bagworm moth makes it possible to visually trace the state of an egg in the egg-holding part during the period from egg-laying to hatch, and makes it possible to promptly detect and cope with the generation of mold, the decomposition and drying of an egg, and the like, if any. Besides, the hatch of a bagworm takes place in several installments over a period of several days. The process until hatching can be visualized, thus making it possible to accurately grasp the starting timing and completion timing of the hatch, and to accordingly prepare a suitable rearing environment preliminarily after hatching.

(1-2) First Instar Bagworm Collection Process

The "first instar bagworm collection process" is a process of collecting, from the egg-holding part, a hatched first instar bagworm in the egg-holding part after the incubating process. The collection method is not limited, and a technology for collecting a first instar silkworm in the sericultural industry can be applied. For example, a first instar bagworm in the egg-holding part may be brushed off using a feather duster or a brush, and transferred to a place where a bagworm is to be grown. After the movement, the first instar bagworm immediately starts producing a nest, utilizing nest materials. This makes it possible to obtain a large number of first instar bagworms, which is difficult for a conventional technology.

(2) Method of Collecting Egg from Egg Collection Device For Bagworm Moth

This method is a method in which a bagworm moth egg obtained by the egg collection method of bagworm moth in the third aspect using the egg collection device for bagworm moth according to the first aspect is collected from the egg-holding part of the egg collection device for bagworm moth, and controlled outside until hatching, and the bagworm after hatching is collected during the first instar stage. This method comprises an egg collection process and an incubating process as essential processes, and in addition, a first instar bagworm collection process as an optional process.

(2-1) Egg Collection Process

The "egg collection process" is a process of collecting, from the egg-holding part, eggs obtained by the egg collection method of bagworm moth in the third aspect. In the present process, eggs after the egg-laying process are brought out through the insert hole or another opening of the egg collection device for bagworm moth, and collected. A method of collection from the egg-holding part is not limited. For example, a brushing-off method may be applied, or an egg batch may be scooped up using a tiny spatula like an earpick. Alternatively, the eggs can be washed off from the egg-holding part using water or a buffer, and collected.

(2-2) Incubating Process

The "incubating process" is a process of incubating a bagworm moth egg. The incubating process is, in principle, in accordance with the method described in (1-1) the incubating process, but is different from (1-1) the incubating process in that eggs are incubated outside the egg collection device for bagworm moth, not in the egg-holding part. The method of incubation outside the egg collection device for bagworm moth is not particularly limited, and the incubation is desirably performed in a place in which a suitable humidity is retained to prevent excessive humidification and drying. Examples of the method comprise a method in which eggs collected on paper such as paper for silkworm egg raising are transferred in the form of an egg batch; the incubation is performed at the incubation temperature on paper serving as a seat humidified to prevent drying.

(2-3) First Instar Bagworm Collection Process

Collecting a first instar bagworm after hatching can be performed in accordance with the method described in (1-2) the first instar bagworm collection process. For example, a bagworm may be brushed off using a feather duster or the like, and transferred to a place serving as a rearing bed for a bagworm.

In the present embodiment, bagworm moth eggs collected in the egg collection process are placed, for example, in a rearing container, whereby first instar larvae that have hatched after the incubating process can be obtained in large numbers in the rearing container without being collected. Hence, the present process is an optional process, and may be performed as necessary.

EXAMPLES

Example 1: Artificial Breeding of Bagworm Moth Using Egg Collection Device for Bagworm Moth (Purpose)

To artificially breed a bagworm moth using the egg collection device for bagworm moth according to the present invention.

(Method and Result)

Last instar larvae of *Eumeta japonica* were collected on the field, and allowed to undergo emergence in a natural environment. A male moth and a female moth obtained were used.

For the egg collection device for bagworm moth according to the present invention, a 1.5 mL tube (from Eppendorf SE) from which a cap was cut off was used. When this was done, the inner diameter of the insert hole was 9.7 mm, and the length of the integrated form of the receiving part and the egg-holding part (the length of the long axis of the egg collection device) was 30 mm.

The female moth was removed from the nest and the puparium using scissors and tweezers, and the bottom of the abdomen was inserted through the insert hole of the egg collection device for bagworm moth, and fixed in the egg collection device for bagworm moth (FIG. 3A).

Next, the bottom of the abdomen of the male moth was manually inserted between the abdomen of the female moth and the insert hole (FIG. 3B).

After inserting the abdomen of the male moth between the insert hole and the abdomen of the female moth, the male moth spontaneously stretched its abdomen toward the mating pore of the female moth, and simultaneously, the female moth vermicularly moved its abdomen received in the receiving part, and attracted the bottom of the abdomen of the male moth to the mating pore of the female moth, with the result that mating was established in the receiving part. The 1.5 mL tube was composed of polypropylene that is a translucent material, and thus, it was possible that the establishment of mating in the receiving part was verified by visual observation from the outside (FIG. 3C).

In nature, the opening of the puparium faces downward, as shown in FIGS. 1B and 1C, and thus, the male moth mates always in an upside-down posture. However, the results of Examples shown in FIG. 3C have revealed that a male moth can achieve mating in a posture vertically opposite to the natural posture. This makes it possible to turn the insert hole of the egg collection device upward, and tremendously simplified the operation and control to be performed during mating and after mating.

Example 2: Collection of Bagworm Moth Egg Using Egg Collection Device for Bagworm Moth (Purpose)

To collect a bagworm moth egg using the egg collection device for bagworm moth according to the present invention.

(Method and Result)

Figure 4:
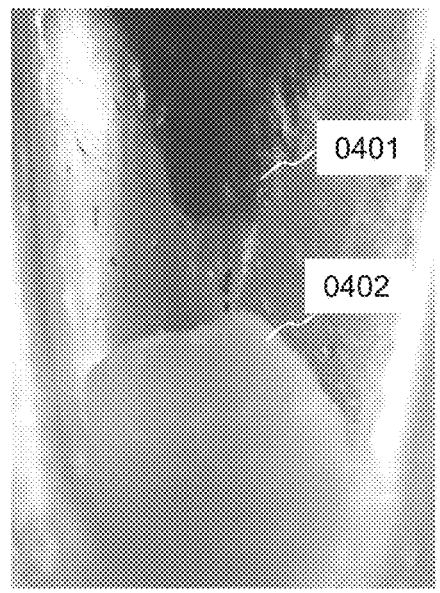
FIG. 4 is a picture showing the bottom (0401) of the abdomen of the female moth of *Eumeta japonica* laying eggs in an egg-holding part of the egg collection device for bagworm moth according to the present invention, and showing an egg batch (0402) obtained by the egg-laying. The egg batch is composed of an average of 1,000 to 3,000 eggs.

A male moth and a female moth of *Eumeta japonica* were bred to each other in the egg collection device for bagworm moth by the method according to Example 1, and then, the male moth was removed manually from the egg collection device. In a state in which the female moth remained in the egg collection device, and where the insert hole of the egg collection device for bagworm moth was turned upward, the female moth was left to stand, incubated at a temperature of 24° C. The female moth started egg laying in the egg-holding part approximately half a day after the establishment of breeding, and another approximately half a day later, approximately 2000 eggs were obtained. FIG. 4 shows the state observed approximately three hours after the start of the egg laying.

Example 3: Mass-Production of First Instar Bagworm (Purpose)

To produce a large number of first instar bagworms from the bagworm moth eggs collected using the egg collection device for bagworm moth according to the present invention.

(Method and Result)

Figure 5:
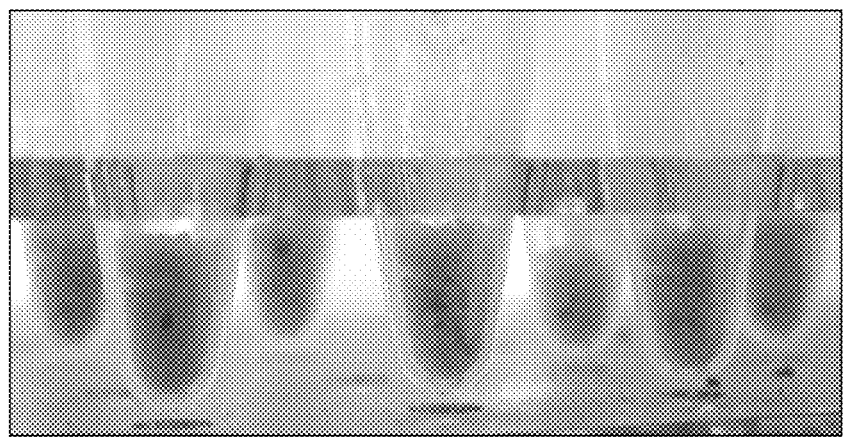
FIG. 5 illustrates pictures showing the production of a first instar bagworm of *Eumeta japonica* using the egg collection device for bagworm moth according to the present invention.
Figure 5:
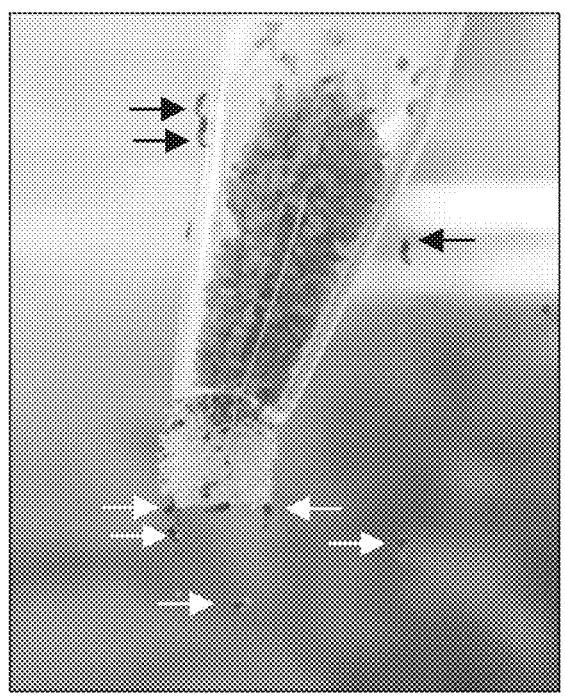

The eggs obtained in Example 2 were incubated in the form of egg batches in the egg-holding part at 24° C. for 21 days, as shown in FIG. 5A. This method made it possible to allow a large number of first instar bagworms of interest to hatch at a high hatching rate of 90% or more (FIG. 5B).

Example 4: Egg Collection Device for Bagworm Moth Comprising Egg-Receiving Means (Purpose)

To verify the influence that the egg-receiving means of the egg collection device for bagworm moth according to the present invention has on egg laying and hatch.

(Method)

For the egg collection device for bagworm moth according to the present invention, a 1.5 mL tube (from Eppendorf SE) from which a cap was cut off was used in the same manner as in Example 1. Into this tube, an 80 mm×80 mm square cut out of a transparent thin-layer film (a food-packaging wrap film: POLY WRAP: from Ube Film, Ltd.: polyethylene) was pushed along the inner wall of the tube, and used as an egg-receiving means. The actual state is shown in FIG. 6A. As a control, a tube comprising no egg-receiving means was used.

The female moth was inserted in the same manner as in Example 1, and allowed to mate with the male moth. Then, evaluations and calculations were made of whether egg laying took place, how visible an egg in the egg-holding part was from the outside, how easy or difficult the collection of eggs was, how many times fertilization took place, how many times hatch was successful, and what the rate of success in hatching was.

(Result)

The results are shown in Table 1.

TABLE 1

| Egg-receiving Means | Number of Samples | Egg-laying | Visibility of Egg | Egg Collection | How Many Times Fertilization Took Place | How Many Times Emergence Was Successful | Rate of Success in Hatch |
|---|---|---|---|---|---|---|---|
| Thin-layer Film | 8 | ○ | ○ | Easy | 7 | 3 | 42.9% |
| None | 6 | ○ | ○ | Difficult | 6 | 4 | 66.7% |

With respect to fertilization, an egg that made it possible to verify the development of the embryo of a bagworm was determined to be a fertilized egg.

The rate of success in hatch was defined as the ratio of how many times hatch was successful to how many times fertilization took place.

Table 1 has revealed that the egg collection device for bagworm moth having an egg-receiving means also has no influence on egg-laying. In addition, the results have also revealed that, as long as the egg-holding part was also composed of a transparent material, the egg-receiving means composed of a transparent material made it possible to verify, from outside, whether and how the egg batch inside the egg-holding part existed. Furthermore, with respect to the collection of an egg in the case of having an egg-receiving means, just pulling the egg-receiving means out of the egg collection device for bagworm moth and spreading the means as shown in FIG. 6E made it possible to collect an egg batch easily. On the other hand, in the case of having no egg-receiving means, an operation such as turning the egg collection device for bagworm moth the other way around, scraping an egg batch out through the insert hole, or the like was necessary but difficult. In addition, the results have revealed that how many times fertilization and hatch were each successful and what rate of success in hatch was determined by the calculation of the number of times gave figures slightly lower than in the case of having no egg-receiving means, but that the egg-receiving means had almost no influence on mating or on the egg after egg-laying.

The above-described results have revealed that in collecting eggs using the egg collection device for bagworm moth according to the present invention, the egg collection device for bagworm moth comprising an egg-receiving means is efficient when an egg batch after egg-laying is collected from the egg collection device for bagworm moth.

All publications, patents, and patent applications cited herein should be incorporated herein by reference in their entirety.

The invention claimed is:

1. A bagworm moth egg collection device composed of a tubular container, comprising:
   an insert hole having an inner diameter into which a female adult of a bagworm moth fits whereby the female adult, bagworm moth is fixed to the bagworm moth egg collection device;
   a receiving part capable of receiving the abdomen of the female adult; and
   an egg-holding part configured to hold eggs obtained by egg-laying.

2. The egg collection device according to claim 1, wherein the egg-holding part has a ventilating means.

3. The egg collection device according to claim 1, wherein the egg-holding part has, therein, a removable egg-receiving means for receiving and collecting the egg obtained by egg-laying.

4. The egg collection device according to claim 1, further comprising a lid configured to occlude the insert hole.

5. The egg collection device according to claim 1, wherein the whole or part of the tubular container comprises a transparent material or a translucent material.

6. The egg collection device according to claim 3, wherein the egg-receiving means consists of a thin-layer film composed of a transparent material or a translucent material.

7. The egg collection device according to claim 1, further comprising an egg-collecting stand configured such that the egg collection device is placed in the egg-collecting stand in such a manner that the insert hole faces upward.

8. A bagworm moth breeding method, comprising:
   inserting the bottom of the abdomen of a female adult of a bagworm moth into an insert hole of the egg collection device for bagworm moth according to claim 1 to fit the abdomen into the insert hole; and
   inserting the bottom of the abdomen of a male adult of a bagworm moth between the insert hole and the abdomen of the female adult to induce mating.

9. The breeding method according to claim 8, wherein the female adult of the bagworm moth is an apterous and apodous morphospecies.

10. The breeding method according to claim 8, wherein the female adult is a virgin.

11. A bagworm moth egg collection method, comprising:
    inserting the bottom of the abdomen of a female adult of a bagworm moth separated from a nest and a puparium into an insert hole of the egg collection device according to claim 1 to fit the abdomen into the insert hole;
    inserting the bottom of the abdomen of a male adult of a bagworm moth between the insert hole and the abdomen of the female adult to induce mating; and
    allowing the female adult to lay eggs in the egg-holding part of the egg collection device.

12. The egg collection method according to claim 11, further comprising removing the female individual after the egg-laying process.

13. A method of producing a first instar bagworm, comprising:
    incubating, in the egg-holding part, the bagworm moth egg obtained by the egg collection method according to claim 11; and
    collecting a hatched first instar bagworm.

14. A method of producing a first instar bagworm, comprising:
    collecting, from the egg-holding part, the bagworm moth egg obtained by the egg collection method according to claim 11; and
    incubating the egg collected.

* * * * *